United States Patent
Barreca et al.

(10) Patent No.: US 11,149,003 B2
(45) Date of Patent: Oct. 19, 2021

(54) RESOLUTION OF RACEMIC BETA-AMINOSULFONE COMPOUNDS

(71) Applicant: Quimica Sintetica, S.A., Barcelona (ES)

(72) Inventors: Giuseppe Barreca, Montevecchia (IT); Giovanni Marras, Galliate (IT); Bruno Romanò, Casatenovo (IT)

(73) Assignee: Quimica Sintetica, S.A., Barcelona (ES)

( * ) Notice: Subject to any disclaimer, the term of this patent is extended or adjusted under 35 U.S.C. 154(b) by 0 days.

(21) Appl. No.: 16/500,671

(22) PCT Filed: Mar. 28, 2018

(86) PCT No.: PCT/EP2018/057898
§ 371 (c)(1),
(2) Date: Oct. 3, 2019

(87) PCT Pub. No.: WO2018/184936
PCT Pub. Date: Oct. 11, 2018

(65) Prior Publication Data
US 2020/0199072 A1 Jun. 25, 2020

(30) Foreign Application Priority Data
Apr. 4, 2017 (EP) .................................... 17382175

(51) Int. Cl.
*C07D 209/48* (2006.01)
*C07C 317/28* (2006.01)

(52) U.S. Cl.
CPC .......... *C07D 209/48* (2013.01); *C07C 317/28* (2013.01)

(58) Field of Classification Search
CPC ............................ C07D 209/48; C07C 317/28
See application file for complete search history.

(56) References Cited

U.S. PATENT DOCUMENTS

| 4,456,595 | A | 6/1984 | Weller, III et al. |
| 6,020,358 | A * | 2/2000 | Muller ..................... A61P 31/00 514/411 |
| 6,962,940 | B2 * | 11/2005 | Muller ..................... A61P 35/00 514/417 |
| 2018/0371013 | A1 * | 12/2018 | Nagahama ............. A61P 25/04 |

FOREIGN PATENT DOCUMENTS

| EP | 2 431 371 A1 | 3/2012 |
| EP | 3 606 908 | 2/2020 |
| WO | WO 2000/025777 A1 | 5/2000 |
| WO | WO 2010/030345 A2 | 3/2010 |
| WO | WO 2013/126360 A2 | 8/2013 |
| WO | WO 2013/126495 A2 | 8/2013 |

OTHER PUBLICATIONS

International Search Report and Written Opinion corresponding to International Application No. PCT/EP2018/057898 dated May 28, 2018.
Intention to Grant a European Patent corresponding to EP 3 606 908 dated Mar. 6, 2020.

* cited by examiner

*Primary Examiner* — Golam M Shameem
(74) *Attorney, Agent, or Firm* — Jenkins, Wilson, Taylor & Hunt, P.A.

(57) ABSTRACT

It is described an industrially viable and advantageous process for the preparation of (S)-beta-aminosulfone (1) starting from the corresponding racemic compound, said (S)-beta-aminosulfone being a useful intermediate for the preparation of N-(2-((1S)-1-(3-ethoxy-4-methoxyphenyl)-2-(methylsulfonyl)ethyl)-2,3-dihydro-1,3-dioxo-1H-isoindol-4-yl)acetamide, also known as Apremilast, the latter being suitable for use in methods of treating, preventing and/or managing psoriasis or psoriatic arthritis.

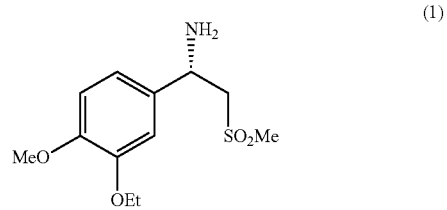

(1)

14 Claims, No Drawings

RESOLUTION OF RACEMIC BETA-AMINOSULFONE COMPOUNDS

FIELD OF THE INVENTION

The present invention provides an industrially viable and advantageous process for the preparation of the (S)-beta-aminosulfone having IUPAC name (S)-2-(3-ethoxy-4-methoxyphenyl)-1-(methylsulphonyl)-eth-2-ylamine and the formula (1) depicted below, starting from the corresponding racemic mixture. Said (S)-beta-aminosulfone is a useful intermediate for the preparation of N-(2-((1S)-1-(3-ethoxy-4-methoxyphenyl)-2-(methylsulfonyl)ethyl)-2,3-dihydro-1,3-dioxo-1H-isoindol-4-yl)acetamide, also known as Apremilast (compound having the formula shown below), the latter being suitable for treating, preventing and/or managing psoriasis or psoriatic arthritis.

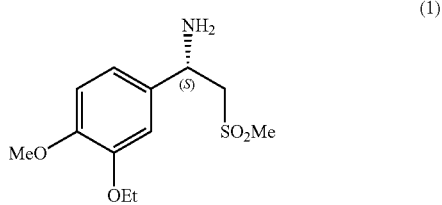

(1)

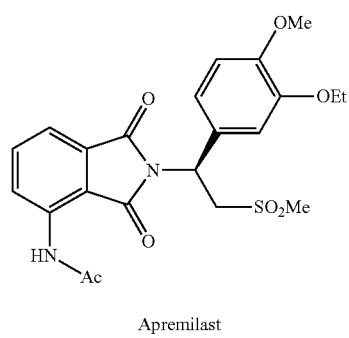

Apremilast

BACKGROUND OF THE INVENTION

Apremilast is a novel, oral small-molecule inhibitor of phosphodiesterase 4 (PDE4) that works intracellularly to modulate a network of pro- and anti-inflammatory mediators. Phosphodiesterase 4 is a cyclic adenosine monophosphate (cAMP)-specific PDE and is the dominant PDE in inflammatory cells. Inhibition of PDE4 elevates intracellular cAMP levels, which in turn downregulates the inflammatory response by modulating the expression of tumor necrosis factor alpha (TNF-α), interleukin (IL)-23, IL-17, and other pro-inflammatory cytokines. Elevation of cAMP also increases anti-inflammatory cytokines. These pro- and anti-inflammatory mediators have been implicated in psoriasis and psoriatic arthritis.

Based on these effects, Apremilast is being developed for use in the treatment of various immune-mediated inflammatory conditions such as psoriasis, rheumatoid arthritis, Behçet disease, and ankylosing spondylitis.

As is the case for the great majority of drugs, Apremilast is a chiral molecule and only the (S)-enantiomer of beta-aminosulfone (1) is useful for preparing it. In general, a mixture of (R,S) enantiomers can contain the two enantiomers in any ratio to each other. The enantiomeric purity is generally expressed as "enantiomeric excess" or ee and is defined, for example for the (S) enantiomer, as [(S−R)/(R+S)]×100, wherein S and R are respectively the amounts of the (S) and (R) enantiomers (as determined for example by GC or HPLC on a chiral stationary phase or polarimetry).

Beta-aminosulfone (1) could be obtained in the desired enantiomeric form (S) either by direct, enantioselective synthesis, or by non-enantioselective synthesis followed by separation of the mixture of enantiomers and isolation of the one of interest. Non-enantioselective synthetic routes lead to a racemic mixture, that is, a mixture in which two possible enantiomers of a compound are present in equal amounts; herein, (1) will designate an enantiomerically pure enantiomer, while with (1') it will be indicated the racemic mixture (racemate) of compound (1), and with (1") an enantiomerically enriched mixture thereof.

Enantioselective processes are based on asymmetric catalysis, such as for example asymmetric catalytic hydrogenation or transfer, asymmetric reductive amination, asymmetric reduction via chiral oxazaborolidine. However, these synthetic routes require the use of expensive materials, e.g. transition metals such as Rh or Ru, and can also be inefficient and inconvenient due to extreme conditions often required (very low temperatures, strictly anhydrous conditions, high pressures), thus limiting the utility of these routes in viable industrial processes. Furthermore, in some cases asymmetric catalysis may lack enantioselectivity so that other steps, e.g. crystallization, are required anyway to obtain the desired optical purity.

Accordingly, in the industry it is generally preferred to adopt non-enantioselective synthetic routes, and isolate the enantiomer of interest at the end of the synthesis with procedures referred to as resolution of the enantiomers mix.

Apremilast and other similar compounds were first described in the international patent application WO 00/25777 A1. The process described therein entails, as key steps, an aldol reaction between 3-ethoxy-4-methoxybenzaldehyde and dimethyl sulfone in the presence of n-butyl lithium, lithium bis(trimethylsilyl)amide and boron trifluoride diethyl etherate; the reaction of N-(1-(3-ethoxy-4-methoxyphenyl)-2-(methylsulfonyl)ethyl)-1,1,1-trimethylsilanamine with hydrochloric acid; the reaction between 1-(3-ethoxy-4-methoxyphenyl)-2-(methylsulfonyl)ethan-1-amine and N-(1,3-dioxo-1,3-dihydroisobenzofuran-4-yl)acetamide, and the final isomers separation by means of chromatography on a chiral stationary phase.

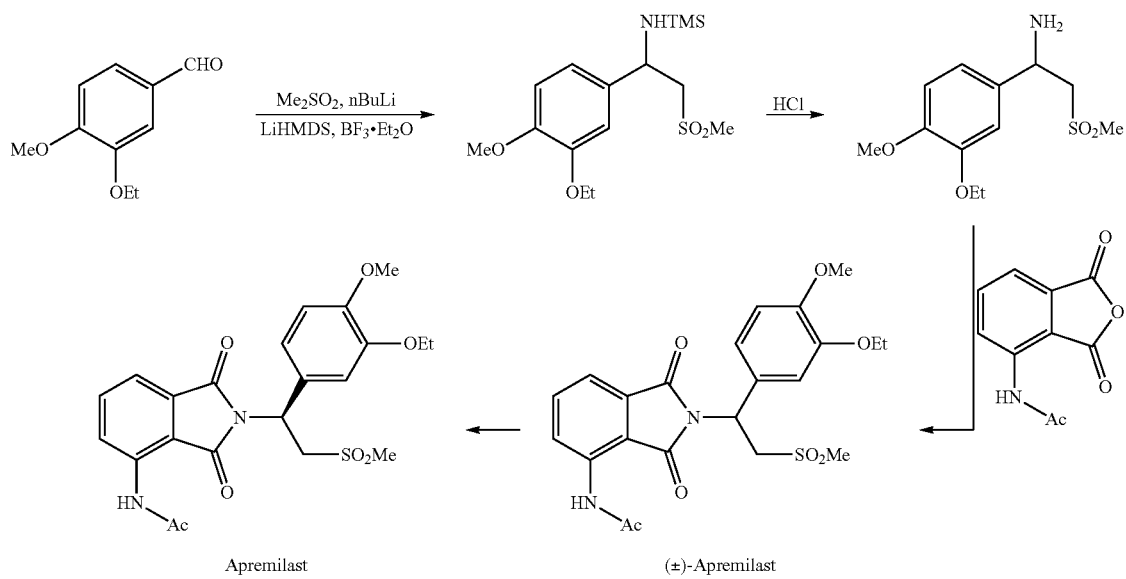

Apremilast    (±)-Apremilast

On industrial scale, the use of this route of synthesis has several drawbacks caused by the poor yield of the aldol reaction or the late stage at which the separation of Apremilast enantiomers is performed. In the latter respect, it is worth noting that, in converting a racemic compound into an enantiomerically pure end product (as in the case of Apremilast), a maximum yield of 50% can be reached thus leading to the loss of at least 50% of the final product.

An alternative process for the preparation of Apremilast involving an optical resolution step has been described in the international application WO 03/080049 A1 by Celgene. According to this patent application a racemic mixture (1') of 1-(3-ethoxy-4-methoxyphenyl)-2-(methylsulfonyl)ethan-1-amine can be optically resolved by treatment with a chiral amino acid salt selected from the group consisting of the L isomers of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, ornithine, 4-aminobutyric acid, 2 amino isobutyric acid, 3 amino propionic acid, norleucine, norvaline, hydroxyproline, sarcosine, citrulline, cysteic acid, tert-butylglycine, tert-butylalanine, phenylglycine, cyclohexylalanine, or preferably N-acetyl-leucine.

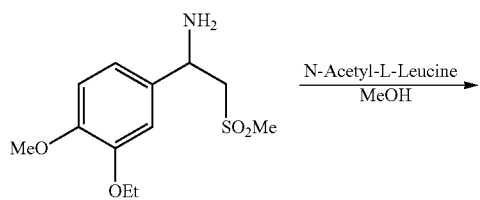

Apremilast

Notwithstanding the vast variety of salts falling within this disclosure, in a later filed experimental report the Applicant of WO 03/080049 A1 compared the use of N-acetyl-L-leucine and N-acetyl-L-phenylalalnine as resolving agents and showed that N-acetyl-L-leucine provided the amino acid salt with 77% ee after a first crystallization while N-acetyl-L-phenylalalnine only provided 14% ee.

A drawback associated with this procedure derives from the use of N-acetyl-L-leucine to separate the two enantiomers of 1-(3-ethoxy-4-methoxyphenyl)-2-(methylsulfonyl)ethan-1-amine, which leads to the isolation, after two crystallization steps, of a product with an enantiomeric excess of 98.5% and an overall yield of 25% (with respect to racemic 1-(3-ethoxy-4-methoxyphenyl)-2-(methylsulfonyl)ethan-1-amine).

Basing on the fact that, in order to comply with ICH specification, all pharmaceutically acceptable compounds should have a purity degree of at least 99.8%, a product having an enantiomeric excess of 98.5% should be subjected to at least one further crystallization step aiming at increasing its purity profile which inevitably results in a further decrease of the overall yield and, as a consequence, in an increased economic impact of the process.

Patent application EP 2431371 A1 describes the resolution of 1-(3-ethoxy-4-methoxyphenyl)-2-(methylsulfonyl)ethan-1-amine (1') via diastereomeric salt formation with N-Acetyl-L-Valine (N-Ac-L-Val) as depicted below:

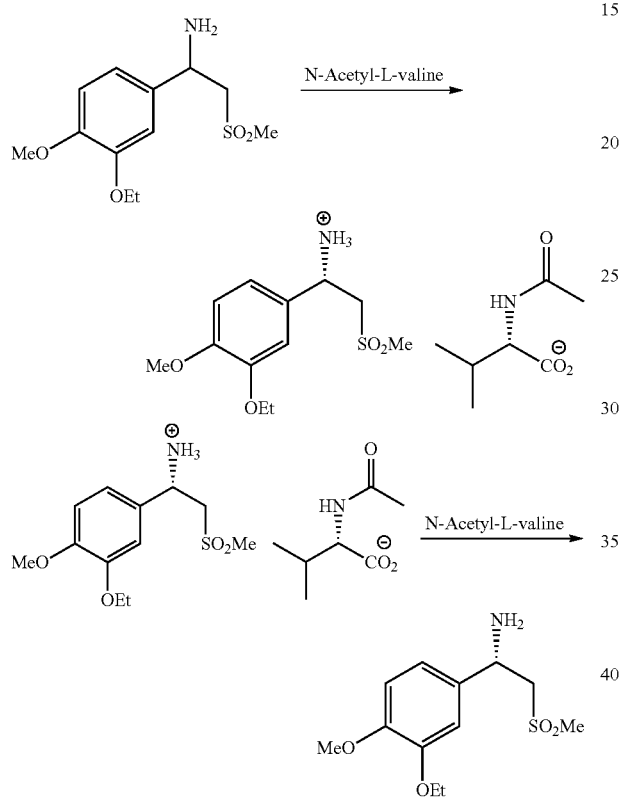

Although no reference to diastereomeric enrichment is made, the process is characterized by low yields, thus limiting its industrial scale-up.

Aim of this invention is to provide a new chemical method to prepare Apremilast or intermediates useful in the synthesis thereof, characterized by high yields and providing the desired compounds with a purity appropriate for the use in pharmaceuticals.

SUMMARY OF THE INVENTION

These objectives are achieved with the present invention which, in a first aspect thereof, relates to a process for the preparation of an enantiomerically pure N-formyl leucine salt of 1-(3-ethoxy-4-methoxyphenyl)-2-(methylsulfonyl)ethan-1-amine (4):

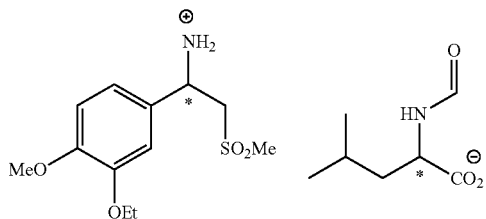

said process comprising the following operations:
a) providing 1-(3-ethoxy-4-methoxyphenyl)-2-(methylsulfonyl)ethan-1-amine in the form of a racemic mixture (1') or in the form of an enantiomerically enriched mixture thereof (1");

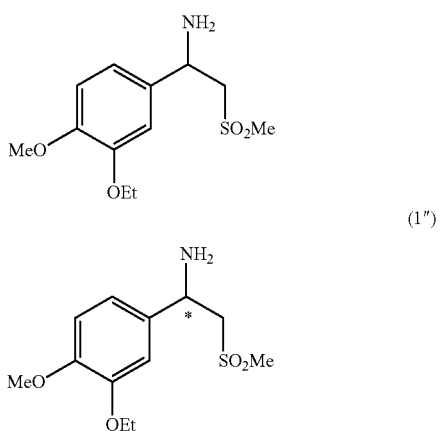

b) optically resolving said racemic (1') or enantiomerically enriched mixture (1") by treatment with an enantiomerically pure N-formyl leucine in the presence of a solvent, to produce the corresponding enantiomerically pure N-formyl-leucine salts (4).

In a possible variant of this aspect of the invention, a further step b') is carried out after step b), comprising deblocking the enantiomerically pure salt (4) prepared in step b) to yield an enantiomerically pure 1-(3-ethoxy-4-methoxyphenyl)-2-(methylsulfonyl)ethan-1-amine (1).

DETAILED DESCRIPTION OF THE INVENTION

All terms used in the present application, unless otherwise indicated, must be interpreted in their ordinary meaning as known in the technical field. Other more specific definitions for some terms used in the present application are given below and are intended to be applied uniformly to the entire description and claims, unless otherwise indicated.

In general, the nomenclature used in this application is based on AUTONOM™ v.4.0, a Beilstein Institute computerized system for the generation of IUPAC systematic nomenclature. If there is a discrepancy between a depicted structure and the name given to that structure, the depicted structure should be considered correct. Furthermore, if the stereochemistry of a structure or a portion of a structure is not indicated with, for example, bold or dashed lines, the structure or portion of the structure has to be interpreted as encompassing all existing stereoisomers of it.

The compounds prepared by the processes of the present invention may have one or more stereogenic centers and may exist and may be used or isolated in enantiomerically pure forms, as enantiomeric enriched mixtures as well as in diastereomerically pure forms or as diastereomeric enriched mixtures. It is to be understood that the processes of the present invention can give rise to any of the previous forms or a combination thereof. It is to be further understood that the products of the processes described herein, can be isolated as enantiomerically and diastereomerically pure forms or as enantiomerically and diastereomerically enriched mixtures.

The term "aryl" refers to any substituent derived from a monocyclic or a polycyclic aromatic hydrocarbon by removal of a hydrogen atom from a ring carbon atom (e.g. phenyl, tolyl, 1-naphtyl or 2-napthyl).

The sign "*" (asterisk) present in some formulae of this description indicates a stereogenic (asymmetric) center, although the absence of asterisks does not necessarily imply that the compound lacks a stereocenter. Such formulae may refer to the racemate or to individual enantiomers or diastereomers, which may or may not be substantially pure.

The term "racemic" refers to a sample of a chiral compound which contains the (+) and (−) isomers in equal amount.

The term "enantiomerically enriched" as used herein means that one of the enantiomers of a compound is present in excess compared to the other enantiomer.

The term "enantiomerically pure" as used herein means that the enantiomeric purity is usually at least about 96%, preferably at least 99%, more preferably at least 99.5%.

The symbol ''''' (dashed bond) present in some of the formulae of the description and the claims indicates that the substituent is directed below the plane of the sheet.

The symbol ━ (wedge bond) present in some of the formulae of the description and the claims indicates that the substituent is directed above the plane of the sheet.

The compounds obtained by the chemical transformations of the present invention can be used in the following steps without further purification or, optionally, can be separated and purified by employing conventional methods well known to those skilled in the art, such as recrystallization, column chromatography, or by transforming them into a salt or in a co-crystal with an appropriate co-former, or by washing with an organic solvent or with an aqueous solution, optionally adjusting pH.

It will be understood that any compound described herein may also describe any salts or co-crystals thereof.

The term "seed" refers to a crystalline substance that is added to a solution of the same substance to induce its crystallization. Seeding with a specific optical isomer often has the useful effect of promoting crystallization of the substance in the same form of the seed.

It should be noted that, during the conversion of the enantiomerically pure 1-(3-ethoxy-4-methoxyphenyl)-2-(methylsulfonyl)ethan-1-amine (1) or the N-formyl-leucine salt thereof (4) into an enantiomerically pure 1,3-dioxoisoindolin-4-ylacetamide (6), no racemization (conversion of the major enantiomer into the minor leading to a lower ee) is observed. Accordingly, the ee detected in the pure 1-(3-ethoxy-4-methoxyphenyl)-2-(methylsulfonyl)ethan-1-amine (1) or in the N-formyl-leucine salt thereof (4), are retained unchanged in the pure 1,3-dioxoisoindolin-4-ylacetamide of formula (6).

According to its most general aspect, the present invention relates to a process for the preparation of an enantiomerically pure N-formyl-leucine salt of 1-(3-ethoxy-4-methoxyphenyl)-2-(methylsulfonyl)ethan-1-amine (4).

The first operation of the process of the invention, a), consists in the provision of a racemic 1-(3-ethoxy-4-methoxyphenyl)-2-(methylsulfonyl)ethan-1-amine (1') or an enantiomerically enriched mixture thereof (1"). This operation can be performed according to two alternative routes of synthesis a.i) and a.ii).

The synthetic route a.i) leads to the preparation of 1-(3-ethoxy-4-methoxyphenyl)-2-(methylsulfonyl)ethan-1-amine in the form of a racemic mixture (1'). This scheme can be, e.g., operated according to the procedures detailed in WO 2010/030345 A2 (via 3-ethoxy-4-methoxybenzonitrile), or, preferably, involves the following steps:

d) reacting 3-ethoxy-4-methoxybenzaldehyde (9) with a compound of formula $R^1$—$NH_2$ and a compound of formula $R^2$—S(O)OH, or a salt thereof to obtain an aminosulfone of formula (2):

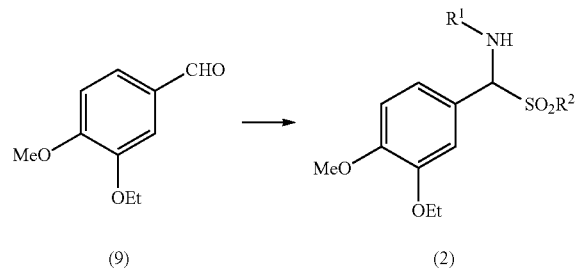

(9)　　　　(2)

wherein:

$R^1$ is an amino protecting group; and $R^2$ is a C1-C6 alkyl, a substituted C1-C6 alkyl, a C6-C10 aryl or a substituted C6-C10 aryl;

e) converting the aminosulfone of formula (2) into a sulfone of formula (3) by treatment with a carbanion derived from dimethyl sulfone:

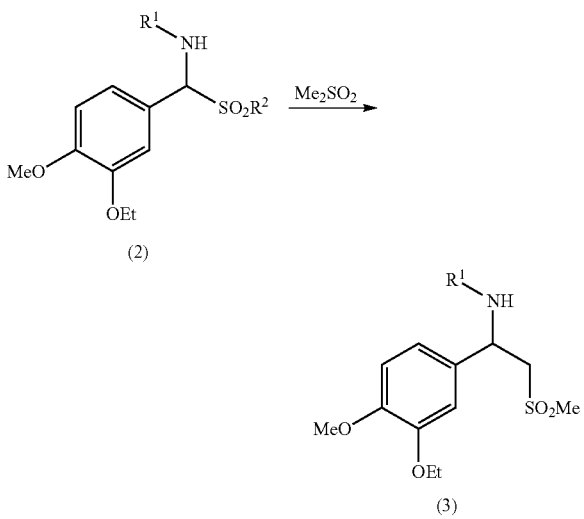

f) deprotecting sulfone (3) to obtain 1-(3-ethoxy-4-methoxyphenyl)-2-(methylsulfonyl)ethan-1-amine in the form of a racemic mixture (1').

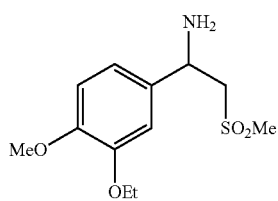
(1')

Amine protecting groups useful for the invention are, for example, carbamates (in which the nitrogen atom is linked to a group of formula —C(O)OR, wherein R is, e.g., methyl, ethyl, tert-butoxy, allyl, benzyl, p-methoxybenzyl, p-nitrobenzyl, p-chlorobenzyl or 2,4-dichlorobenzyl carbamate), amides (in which the nitrogen atom is linked to a group of formula —C(O)-R', wherein R' is for example hydrogen, methyl, chloromethyl, trichloromethyl, trifluoromethyl, phenyl, or benzyl) or phosphinoamides (in which the nitrogen atom is linked to a group of formula —P(O)-(R")$_2$ wherein R' is, for example, aryl, preferably phenyl).

Step d) includes the conversion of 3-ethoxy-4-methoxybenzaldehyde (9) into an aminosulfone of formula (2). This operation can be conveniently carried out by reacting 3-ethoxy-4-methoxybenzaldehyde (9) with a compound of formula $R^1$—NH$_2$ and a compound of formula $R^2$—S(O)OH or a salt of the compound of formula $R^2$—S(O)OH, wherein the substituents assume the meanings reported above. Step d) is conveniently carried out in the presence of an acid, preferably selected from the group consisting of a Lewis acid (more preferably chlorotrimethylsilane) and a carboxylic acid (more preferably formic acid).

Preferably step d) is carried out in the presence of a salt of the compound of formula $R^2$—S(O)OH (generally referred to as sulfinate). More preferably, said sulfinate is a compound of formula $R^2$—S(O)OM, wherein the substituents assume the meanings reported above and M is an ion, such as sodium, potassium, lithium, calcium, magnesium, copper or caesium. Even more preferably said salt of the compound of formula $R^2$—S(O)OH is sodium p-toluenesulfinate.

The compound of formula $R^1$—NH$_2$ is preferably selected from the group consisting of carbamates (preferably tert-butyl or benzyl carbamate), amides (e.g. formamide or acetamide), phosphinoamides (preferably diphenylphosphinoamide) or mixtures thereof.

Preferably, step d) is carried out in at least one solvent, more preferably in a mixture comprising water and at least one solvent selected from the group consisting of alcoholic solvents (for example methanol, ethanol, 2-propanol, 1-butanol, 2-butanol, tert-butanol and mixtures thereof) and ethers (for example tetrahydrofuran). According to a preferred embodiment of this aspect of the invention, step d) is carried out in a mixture comprising an alcohol (preferably 1-butanol) and water, said mixture having, in an even more preferred embodiment, a ratio of the alcoholic solvent to water from about 1:0.5 vol/vol to about 1:10 vol/vol. Preferably, the ratio of alcoholic solvent to water is from about 1:2 vol/vol to about 1:4 vol/vol.

In step d) the reaction temperature can be between from 0° C. to 40° C., preferably from about 10° C. to about 20° C. In general, the higher the reaction temperature, the shorter the reaction time.

The amount of acid optionally used in step d) (preferably a Lewis or a carboxylic acid) is conveniently from about 1 to about 2 equivalents, preferably from 1.05 to 1.50 equivalents, more preferably from 1.10 to 1.40, even more preferably from 1.15 to 1.35, with respect to the molar quantity of the starting aldehyde (9).

The compound of formula $R^2$—S(O)OH or the salt thereof are used in step d) in amounts conveniently from 1 to 2 equivalents, preferably from 1.01 to 1.50 equivalents, more preferably from 1.05 to 1.40, even more preferably from 1.08 to 1.35, with respect to the molar quantity of the starting aldehyde (9).

The amount of the compound of formula $R^1$—NH$_2$ used in step d) is conveniently from 1 to 2 equivalents, preferably from 1.01 to 1.50 equivalents, more preferably from 1.05 to 1.40, even more preferably from 1.08 to 1.35, with respect to the molar quantity of the starting aldehyde (9).

The inventors have observed that, in the reaction mixture, aminosulfone (2) is in equilibrium with the starting aldehyde (9), and that the equilibrium can be shifted towards the reaction aminosulfone (2) by allowing this compound to crystallize out from the reaction mixture, thus leading the reaction to substantial completion.

Said crystallization conditions may be easily determined by a person skilled in the art by means of a preliminary investigation including dispersing the aminosulfone (2) into the selected solvent or mixture of solvents used in step d) so as to determine its solubility equilibrium.

In one embodiment of this aspect of the invention, the precipitated aminosulfone (2) is triturated and finally washed with iso-propyl acetate and subsequently converted into a sulfone of formula (3).

The aminosulfone of formula (2) thus obtained, optionally isolated, is further converted into a sulfone of formula (3), according to step e).

Step e) can be performed by treating the aminosulfone of formula (2), optionally converted into the corresponding imine (10) as detailed below, with a carbanion of dimethyl sulfone. This step can be carried out in any suitable solvent, such as ethers (preferably diethyl ether, tetrahydrofuran, 2-methyltetrahydrofuran, methyl tert-butyl ether), N-methyl pyrrolidone, N,N-dimethylacetamide, N,N-dimethylformamide, glyme, diglyme, toluene, xilene, hexane or mixtures thereof; at a temperature from −80 to −30° C., preferably from −60 to −50° C., e.g. at −55° C.

The carbanion of dimethyl sulfone can be prepared according to standard techniques in organic synthesis, for example, by treating dimethyl sulfone with a strong base. Suitable strong bases are preferably selected from the group consisting of organolithium reagents, organomagnesium reagents or sodium, lithium, potassium or magnesium amides. The preparation of the carbanion of dimethyl sulfone normally takes place at a temperature of from −80 to −30° C., for example from −60 to −50° C., in an ether (preferably tetrahydrofuran, diethyl ether, 2-methyltetrahydrofuran, methyl tert-butyl ether, bis(2-methoxyethyl) ether) optionally in mixture with a hydrocarbon, aliphatic or aromatic (preferably hexane, toluene, or xylene). Preferably, the solvent used is a mixture of tetrahydrofuran and n-hexane.

Organolithium reagents useful for this purpose are for example n-butyllithium, secbutyllithium, phenyllithium, neopentyllithium, propyllithium, tert-butyllithium or preferably hexyllithium; organomagnesium reagents are for example a tert-butylmagnesium or iso-propylmagnesium halide (preferably tert-butylmagnesium or iso-propylmagnesium chloride); lithium, sodium, potassium or magnesium amides are for example selected from the group comprising sodium, lithium or potassium bis(trimethylsilyl)amides (NaHMDS, LiHMDS or KHMDS), lithium diisopropylamide (LDA) or magnesium bis(diisopropylamide) (MDA).

In the case when an organomagnesium reagent is used to prepare the carbanion of dimethyl sulfone, convenient reaction conditions include the presence of at least one alkali halide (preferably a chloride), for example a lithium, sodium, potassium or caesium chloride, or of a halide of zinc or copper. More preferably the carbanion of dimethyl sulfone is prepared by means of a mixture of iso-propylmagnesium chloride and lithium chloride.

Alternatively said carbanion can be prepared by treating dimethyl sulfone with a hydride (preferably sodium, lithium or potassium hydride) or an alkali metal tert-butoxide (such as sodium or potassium tert-butoxide) at a temperature from −40 to 50° C., for example from −30 to 40° C., in an ether (preferably tetrahydrofuran), in N,N-dimethylacetamide or in N,N-dimethylformamide.

The strong base is preferably used in stoichiometric amount with respect to the molar amount of dimethyl sulfone used.

The molar ratio of the carbanion of dimethyl sulfone with respect to the aminosulfone of formula (2) is normally from 1 to 6, preferably from 3 to 4.

In a possible variant of this operation, the aminosulfone of formula (2) is converted into the corresponding imine (10):

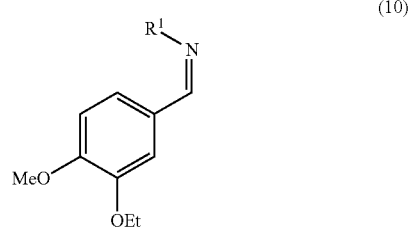

wherein $R^1$ can assume any of the meanings given above; which is subsequently treated with the carbanion of dimethyl sulfone.

Said imine (10) can be, for example, prepared by treating the aminosulfone (2) with one of the bases listed above to operate step e). Alternatively said step can be performed by treating the aminosulfone (2) with a hydroxide or a carbonate of an alkali metal (such as $K_2CO_3$, $Na_2CO_3$, $Li_2CO_3$, $Cs_2CO_3$, KOH, NaOH, LiOH) in a water miscible solvent (e.g. methanol, ethanol, tetrahydrofuran, dimethoxyethane, dioxane or a mixture thereof) optionally in mixture with water. The amount of the hydroxide or carbonate of the alkali metal used is normally from 1 to 5 equivalents, preferably from 1.5 to 2 equivalents, compared to the molar quantity of the aminosulfone (2) used.

Preferably the carbanion of dimethyl sulfone used in step e) is $LiCH_2SO_2Me$, more preferably, $LiCH_2SO_2Me$ prepared in situ by reacting $Me_2SO_2$ with nBuLi or, even more preferably, with nHexLi.

Preferably, in the case when nHexLi is used to prepare the carbanion of dimethyl sulfone, the ratio of intermediate (2) to dimethyl sulfone and nHexLi is from about 1:2:2 to about 1:6:6 on molar basis, preferably about 1:4:4 on molar basis.

The following step f), entails the conversion of sulfone (3), optionally isolated, into a racemic mixture of 1-(3-ethoxy-4-methoxyphenyl)-2-(methylsulfonyl)ethan-1-amine (1'). This operation can be performed using any one of the methods generally known in the field to remove an amino protecting group, for example one of those described in Theodora W. Green, *Protective Groups in Organic Synthesis*, John Wiley & Sons (1999), pages 503-598, which are herein incorporated by reference. Preferably, in the case where $R^1$ forms, together with the nitrogen atom to which it is linked, a carbamate group, said de-protection step may be operated according to the procedures detailed on pages 504-540 of the text referred to above, while, in the case where $R^1$ forms, together with the nitrogen atom to which it is linked, an amide or a phosphinoamide group, said de-protection step can be carried out according to the procedures reported respectively on pages 551-561 and 598 of the same text. According to an even more preferred embodiment of this aspect of the invention, in the case where $R^1$ is a benzyloxycarbonyl, step f) can be carried out by treatment with hydrogen in the presence of a catalyst (e.g. palladium, platinum or nickel) optionally supported on an appropriate carrier, such as carbon or barium carbonate in an alcohol (preferably methanol or ethanol) or a mixture thereof with water. Conversely, when $R^1$ is a tert-butoxycarbonyl group, it can be carried out according to one of the procedures described in Theodora W. Green, *Protective Groups in Organic Synthesis*, John Wiley & Sons (1999), pages 520-522. Preferably step f) is performed by treating sulfone (3) with a solution of hydrogen chloride in water or in an organic solvent.

The alternative synthetic route a.ii) leads to the preparation of an enantiomerically enriched mixture of 1-(3-ethoxy-4-methoxyphenyl)-2-(methylsulfonyl)ethan-1-amine (1"). This step can be carried out according to procedures known in the art, for example those detailed in WO 2013/126360 A2 or in WO 2013/126495 A2.

The optionally isolated 1-(3-ethoxy-4-methoxyphenyl)-2-(methylsulfonyl)ethan-1-amine (1') or (1") provided in step a), is subsequently treated, according to step b), with an enantiomerically pure N-formyl leucine, preferably N-formyl-L-leucine, in the presence of a solvent to obtain the corresponding diastereomeric N-formyl leucine salts which are finally optically purified by diastereomeric salt resolution to the enantiomerically pure N-formyl-leucine salt of 1-(3-ethoxy-4-methoxyphenyl)-2-(methylsulfonyl)ethan-1-amine (4).

The formation and fractionation of the diastereomeric salts are generally performed by heating to a temperature next to the boiling point of the used solvent, followed by cooling to a temperature between 0 and 40° C., preferably between 10 and 30° C. The formation of the salt is complete within some minutes but the reaction time can be extended to several hours without causing any disturbance. The molar ratio of N-formyl leucine with respect to 1-(3-ethoxy-4-methoxyphenyl)-2-(methylsulfonyl)ethan-1-amine (1') or (1") is normally from 0.5 to 1.5, preferably 1. Examples of solvents suitable for the formation and fractionation of the salts are alcohols (e.g. ethanol, 2-propanol, 1-butanol, 2-butanol, or preferably methanol) optionally in mixture with water.

The volume of the solvent is normally from 5 mL to 20 mL per gram of 1-(3-ethoxy-4-methoxyphenyl)-2-(methylsulfonyl)ethan-1-amine (1') or (1") used; preferably, said volume is from 6 to 12 mL per gram of 1-(3-ethoxy-4-methoxyphenyl)-2-(methylsulfonyl)ethan-1-amine (1') or (1"), even more preferably from 8 to 11 mL.

In a possible variant of this operation, a seed of the desired optically active isomer is added to the solution of the diastereomeric salts before cooling it down.

If the enantiomeric excess of the N-formyl leucine salt (4) is not yet suitable for the intended use, hot-trituration is carried out, according to step g), at reflux temperature in the same alcoholic solvents used to perform step b), preferably in methanol. During said hot-trituration, the ratio of alcoholic solvent to the N-formyl leucine salt (4) is from 6:1 v/w to 4:1 v/w, preferably from 5:1 v/w to 4.5:1 v/w.

A variant of the process object of this aspect of the invention includes an additional step b'), carried out after step b), comprising deblocking the enantiomerically pure salt (4) recovered in step b) to yield the corresponding enantiomerically pure 1-(3-ethoxy-4-methoxyphenyl)-2-(methylsulfonyl)ethan-1-amine (1). Preferably, said deblocking is carried out by contacting the pure salt prepared in step b) with a hydroxide or a carbonate of an alkali metal (such as $K_2CO_3$, $Na_2CO_3$, $Li_2CO_3$, $Cs_2CO$, KOH, NaOH, LiOH) in water or in a mixture comprising water and at least one solvent, preferably selected from the group consisting of water miscible solvents (e.g. methanol, ethanol, tetrahydrofuran, dioxane and a mixture thereof); ethers (e.g. tetrahydrofuran, 2-methyltetrahydrofuran); esters (e.g. ethyl acetate, iso-propyl acetate, n-propyl acetate, n-butyl acetate); aliphatic or aromatic hydrocarbons (e.g., hexane, heptane or toluene) and halogenated solvents (preferably dichloromethane). The amount of the hydroxide or carbonate of the alkali metal used is normally from 1 to 5 equivalents, preferably from 1.05 to 4 equivalents, more preferably from 1.1 to 3 equivalents, compared to the molar quantity of the enantiomerically pure salt (4).

According to an alternative and preferred embodiment of this aspect of the invention, the deblocking of step b') is performed in water at a temperature from 20 to 100° C. Even more preferably the deblocking of step b') is carried out in water at a temperature from 40 to 100° C. followed by cooling to a temperature from 0 to 35° C. in order to promote the crystallization of the enantiomerically pure 1-(3-ethoxy-4-methoxyphenyl)-2-(methylsulfonyl)ethan-1-amine (1).

In another preferred embodiment of the invention, the enantiomerically pure N-formyl-leucine salt (4) prepared in step b), or the enantiomerically pure 1-(3-ethoxy-4-methoxyphenyl)-2-(methylsulfonyl)ethan-1-amine (1) produced in step b') are further reacted, in an optional step c), with N-(1,3-dioxo-1,3-dihydroisobenzofuran-4-yl)acetamide (5) to produce an enantiomerically pure 1,3-dioxoisoindolin-4-ylacetamide of formula (6), a co-crystal, a solvate or a hydrate thereof:

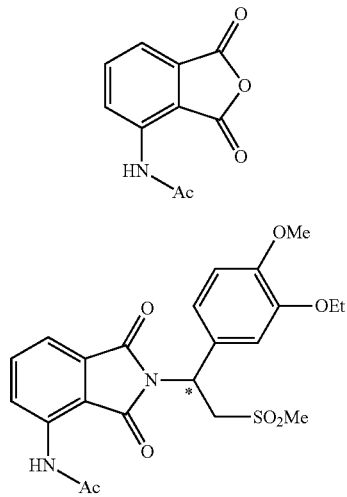

N-(1,3-dioxo-1,3-dihydroisobenzofuran-4-yl)acetamide (5) used as reagent in this step is commercially available; alternatively, it can be prepared according to standard techniques in organic synthesis, for example according to the procedure described in U.S. Pat. No. 4,456,595 A.

The coupling between the pure 1-(3-ethoxy-4-methoxyphenyl)-2-(methylsulfonyl)ethan-1-amine (1) or the pure N-formyl leucine salt (4) and N-(1,3-dioxo-1,3-dihydroisobenzofuran-4-yl)acetamide (5) is carried out, in optional step c), at a temperature from 30° C. to the boiling point of solvent used, preferably from 40 to 90° C., for example at 75° C., in a suitable solvent, preferably a mixture of N,N-dimethylacetamide and acetic acid.

The amount of N-(1,3-dioxo-1,3-dihydroisobenzofuran-4-yl)acetamide (5) is normally from 1 to 2 equivalents, preferably from 1.03 to 1.05 equivalents, with respect to the molar quantity of the enantiomerically pure 1-(3-ethoxy-4-methoxyphenyl)-2-(methylsulfonyl)ethan-1-amine (1) or of the pure salt (4).

In a more preferred embodiment thereof, the process object of this aspect of the invention may comprise a further optional step h) including the crystallization of the enantiomerically pure 1,3-dioxoisoindolin-4-ylacetamide of formula (6) prepared according to step c).

Said crystallization is generally performed by heating a solution of the 1,3-dioxoisoindolin-4-ylacetamide of formula (6) to a temperature next to the boiling point of the used solvent, followed by cooling to a temperature from 0 to 30° C. Examples of solvents suitable for the aim are water; alcohols (e.g. methanol, ethanol); hydrocarbons, either aliphatic or aromatic (preferably hexane, heptane or toluene); acetates (preferably ethyl acetate or iso-propylacetate); ethers (preferably methyl tert-butyl ether or tetrahydrofuran); ketones (preferably acetone or 2-butanone); chlorinated solvents (preferably dichloromethane) and mixtures thereof.

Preferably the enantiomerically pure N-formyl-leucine salt of 1-(3-ethoxy-4-methoxyphenyl)-2-(methylsulfonyl) ethan-1-amine (4), prepared in operation b) of the process, is a N-formyl-L-leucine salt of formula (4A):

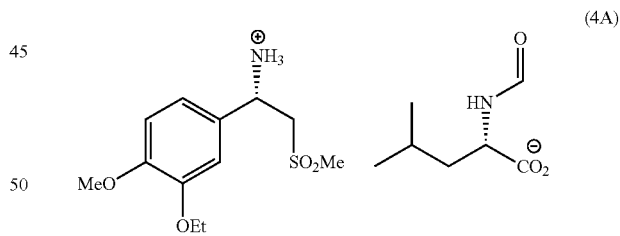

In this case, the process of the invention leads, after the optional step c), to the formation of Apremilast, a co-crystal, a solvate or a hydrate thereof.

In another embodiment thereof, this aspect of the invention relates to a process for preparing an enantiomerically pure 1,3-dioxoisoindolin-4-ylacetamide of formula (6) (preferably Apremilast), a co-crystal, a solvate or a hydrate thereof, comprising reacting 1-(3-ethoxy-4-methoxyphenyl)-2-(methylsulfonyl)ethan-1-amine (1) or its N-formyl leucine salt (4) with N-(1,3-dioxo-1,3-dihydroisobenzofuran-4-yl)acetamide (5).

The process of the present invention reaches the proposed object since, surprisingly, it only requires one crystallization and one hot-trituration of the N-formyl-leucine salt of 1-(3- ethoxy-4-methoxyphenyl)-2-(methylsulfonyl)ethan-1-amine (4) to achieve a beta-aminosulfone (1) with an optical purity suitable for pharmaceutical uses. In comparison, the process of WO 03/080049 A1, besides higher volumes of solvent, requires more than two crystallization stages of the corresponding diastereomeric salt to achieve the same object. It is thus surprising that a noteworthy improvement of yield of the resolution of the racemic mixture can be obtained simply changing the radical linked to the nitrogen atom of leucine, from acetyl to formyl.

Use of the enantiomerically pure 1-(3-ethoxy-4-methoxyphenyl)-2-(methylsulfonyl)ethan-1-amine (1) to directly prepare Apremilast is advantageous, since Apremilast can be isolated by precipitation induced by dilution with an anti-solvent when the reaction reaches its substantial completion.

The invention will be further illustrated by the following Examples.

EXAMPLE 1

Resolution of Racemic Mixture (1') with N-Formyl-L-Leucine (N-CHO-L-Leu).

In a 3 L glass jacketed reactor, equipped with mechanical stirrer, thermometer, condenser and kept under inert gas, were charged at 20-25° C. racemic beta-aminosulfone (1') (200 g, 0731 moles), N-Formyl-L-Leucine (115 g, 0.722 moles) and methanol (2200 mL). Under stirring, the temperature was brought up to reflux of the system (about 65° C.) and maintained in these conditions until a solution was obtained. The solution was then allowed to cool down to 40° C., and then maintained under stirring at 40° C. until the formation of a thick suspension was observed. The suspension was heated up to 45-47° C. in order to homogenize the mass for additional 30 minutes and then cooled down to 20-25° C. over a period of three-four hours. The solid was filtered by means of a Buckner funnel and washed with cold methanol (3×100 ml). The wet cake was oven-dried at 45-50° C. under reduced pressure until constant weight, thus giving 110 g (0.256 moles) of the crude product (molar yield from racemic beta-aminosulfone 35.0%, 97.6% ee, S:R 98.8:1.2).

The crude solid (110 g) was mixed with 500 mL of fresh methanol and the mixture was brought up to reflux temperature (65° C.) and maintained under these conditions for two hours. The slurry was then cooled down to 20-25° C. over a period of three-four hours and maintained under these conditions for additional two hours. The suspension was finally filtered by means of a Buckner funnel and washed with methanol (3×100 ml). The wet cake was oven-dried at 45-50° C. under reduced pressure until constant weight, thus giving 95 g (0.220 moles) of the diastereomeric salt (4') (99.8% ee, S:R 99.9:0.1, total molar yield from racemic beta-aminosulfone: 30%).

EXAMPLE 2

This example is representative of step d) of the present invention.

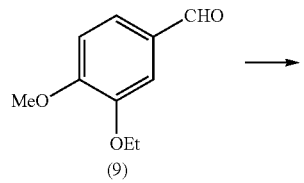

(9)

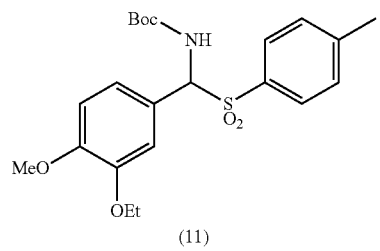

(11)

In a 3 L glass jacketed reactor, equipped with mechanical stirrer, thermometer, condenser and kept under inert gas, were charged at 20-25° C. 3-ethoxy-4-methoxybenzaldehyde (200 g), tert-butyl carbamate (144 g), sodium p-toluenesulfinate (216 g), 1-butanol (130 mL) and water (1080 mL). Addition of the solvents onto the solids resulted in a latent endotherm of the system (endothermic dissolution). Under stirring, the temperature was adjusted at 20-25° C., 68 g of formic acid were added and the system was maintained under these conditions for additional 48 hours, in order for the intermediate product (11) to precipitate abundantly. The system was then diluted with 800 mL of water and maintained under stirring for additional 24 hours.

After cooling down to 0-5° C., a 15% (w/w) sodium hydrogen carbonate aqueous solution up to a stable pH of 7.0-7.3 was slowly added to the suspension. The resulting mixture was finally filtered under reduced pressure and the wet cake washed with 3×100 mL of water. The wet solid was charged in the same reactor again, and 1200 mL of isopropyl acetate were added. The resulting suspension was stirred for one hour at 20-25° C., then filtered and the wet cake washed with 3×60 mL of isopropyl acetate. The final product was dried under vacuum at 40° C., thus affording 300 g of intermediate (11).

EXAMPLE 3

This example is representative of steps e) and f) of the present invention.

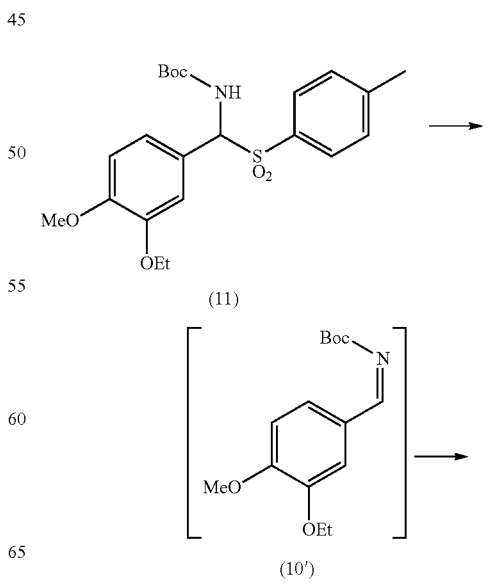

(11)

(10')

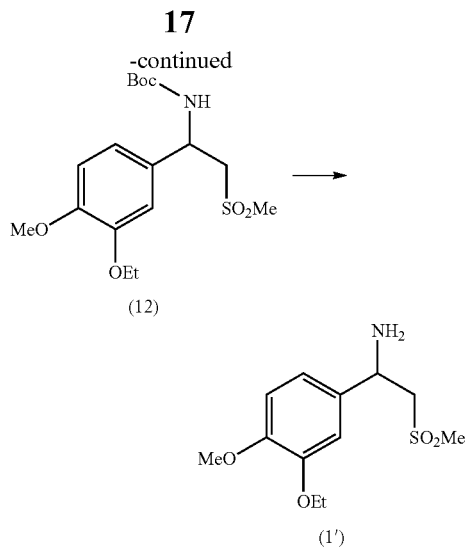

(12)

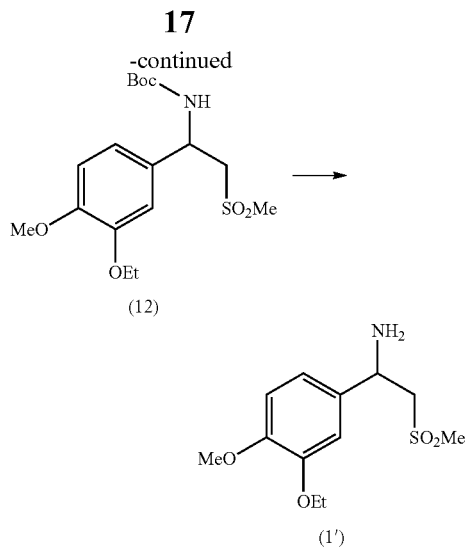

(1')

Dimethyl sulfone (310 g) and tetrahydrofuran (1800 mL) were charged at 20-25° C. to a 10 L glass jacketed reactor equipped with mechanical stirrer, thermometer, condenser and kept under inert gas. Resulting suspension was cooled down to −60° C. Under stirring, n-hexyl lithium (2.3 M solution in hexane, 1440 mL) was added at a rate such that the reaction temperature did not exceed −40° C. (exothermic reaction). A previously prepared solution of activated intermediate (11) (360 g) in tetrahydrofuran (3600 mL) was then added to the reactor at such a rate that the reaction temperature did not exceed −55° C. At the end of the addition, the system was maintained at −55° C. for one additional hour. Then the mass was quickly poured into another reactor containing 1260 mL of water at 20-25° C. The reactor was rinsed with 360 mL of tetrahydrofuran and the rinsing was combined to the quenched mixture. Temperature of the mass was adjusted to 20-25° C. and the layers were allowed to separate. Bottom aqueous phase was transferred into another suitable reactor and counter-extracted with 540 mL of toluene at 45-50° C. Combined organic layers were concentrated under reduced pressure (25-40 mbar; T=50-55° C.) down to a viscous residue.

After having added toluene (1080 mL), water (270 mL) and hydrochloric acid (12N, 170 g), the resulting solution was heated up to 65-70° C. and maintained under stirring at these conditions for additional one hour. The mixture was cooled down to 25-30° C. and the layers were allowed to separate. Bottom aqueous layer was transferred into another reactor, where 1440 mL of 1-butanol and 240 g of 30% (w/w) sodium hydroxide aqueous solution were added, keeping the internal temperature below 50° C. Temperature of the mass was adjusted to 45-50° C. and the layers were allowed to separate. Bottom aqueous phase was transferred into another suitable reactor and counter-extracted with 180 mL of 1-butanol. Combined organic layers were concentrated under reduced pressure (25-40 mbar; T=55-60° C.) to a viscous residue. The mass was diluted with 540 mL of 1-butanol, heated up to 75-80° C. and filtered through a celite pad in order to remove insoluble particles. Reactor and lines were rinsed with 180 mL of 1-butanol and the combined alcoholic phases were allowed to cool down to 0-5° C. in order for compound (1') to crystallize. The obtained solid was filtered, the wet cake washed with 2×180 mL of 1-butanol and the final product dried under vacuum at 45-50° C., thus affording 145 g of compound (1').

$^1$H NMR (CDCl$_3$): δ1.43-1.46 (t, 3H), 2.88 (s, 3H), 3.18-3.32 (m, 2H), 3.83 (s, 3H), 4.07-4.11 (q, 2H), 4.55-4.58 (d, 1H), 6.81-6.89 (m, 3H), 8.71 (2H).

EXAMPLE 4

This example is representative of additional step b') of the present invention.

To a solution of sodium carbonate (17.5 g, 165 mmol) in water (220 mL) at 20-25° C., N-Formyl-L-Leucine salt (4') (65.0 g, 150 mmol) was added under stirring. The mixture was heated to 65-70° C. until a solution was obtained then it was cooled to 50-55° C. and maintained under the same conditions until crystallization occurred (about 30 minutes). The suspension was cooled to 25° C. over 3-4 hours, and the solid filtered and washed with water. The solid was dried under reduced pressure at 55° C. to yield 40 g of enantiomerically pure 1-(3-ethoxy-4-methoxyphenyl)-2-(methylsulfonyl)ethan-1-amine (1) (97% yield from salt 4').

The invention claimed is:

1. A process for preparing an enantiomerically pure N-formyl leucine salt of 1-(3-ethoxy-4-methoxyphenyl)-2-(methylsulfonyl)ethan-1-amine of formula (4):

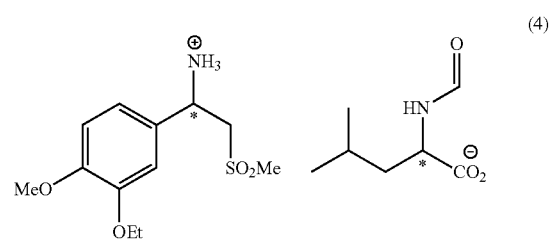

(4)

the process comprising the steps of:
providing 1-(3-ethoxy-4-methoxyphenyl)-2-(methylsulfonyl)ethan-1-amine in the form of a racemic mixture of formula (1') or in the form of an enantiomerically enriched mixture thereof of formula (V);

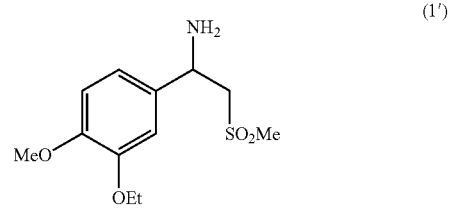 [SMILES: CCOc1cc(C(N)CS(C)(=O)=O)ccc1OC]

(1')

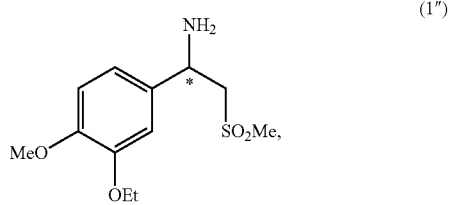

(1")

and
optically resolving said racemic mixture of formula (1') or enantiomerically enriched mixture of formula (1") by treatment with an enantiomerically pure N-formyl leucine in the presence of a solvent to produce the corresponding enantiomerically pure N-formyl-leucine salt of formula (4) with an enantiomeric purity of at least 99%.

2. The process according to claim 1, wherein the process further comprises preparing the racemic mixture of 1-(3-ethoxy-4-methoxyphenyl)-2-(methylsulfonyl)ethan-1-amine of formula (1') according to the following steps:

reacting 3-ethoxy-4-methoxybenzaldehyde of formula (9) with a compound of formula R¹—NH₂ and a compound of formula R²—S(O)OH, or a salt thereof, to obtain an aminosulfone of formula (2):

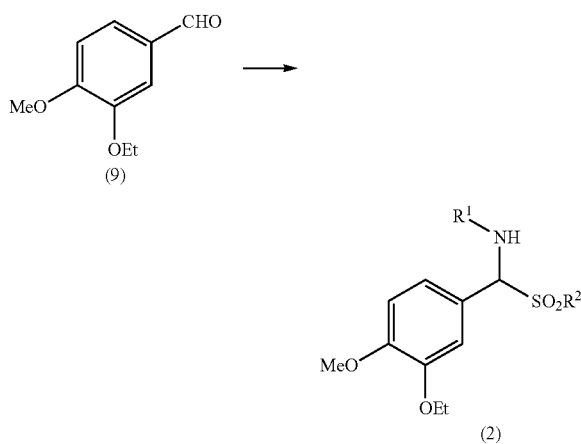

wherein:
R¹ is an amino protecting group; and
R² is a C1-C6 alkyl, a substituted C1-C6 alkyl, a C6-C10 aryl or a substituted C6-C10 aryl;

converting the aminosulfone of formula (2) into a sulfone of formula (3) by treatment with a carbanion derived from dim ethyl sulfone:

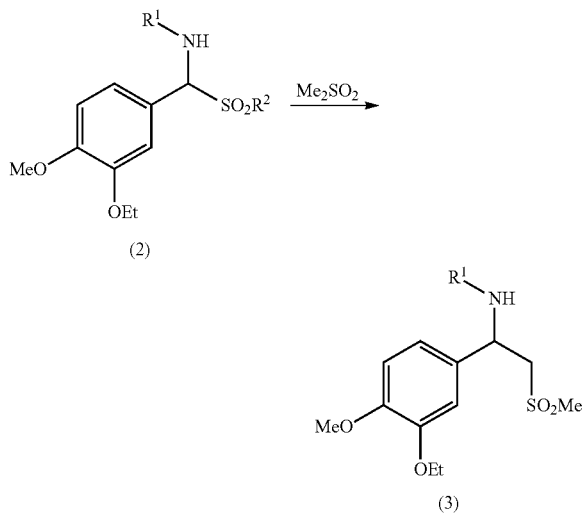

deprotecting the sulfone of formula (3) to obtain 1-(3-ethoxy-4-methoxyphenyl)-2-(methylsulfonyl)ethan-1-amine of formula (1') in the form of a racemic mixture:

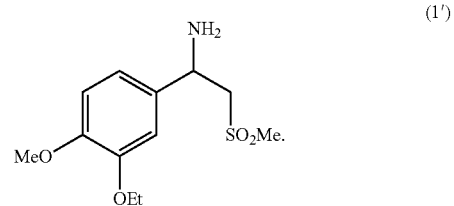

3. The process according to claim 1, further comprising adding a seed of the desired optically active isomer during the optically resolving step.

4. The process according to claim 1, wherein a volume of solvent used in the optically resolving step is between 5 mL and 20 mL per gram of 1-(3-ethoxy-4-methoxyphenyl)-2-(methylsulfonyl)ethan-1-amine of formula (1') or of formula (1").

5. The process according to claim 1, wherein a molar ratio of N-formyl leucine with respect to 1-(3-ethoxy-4-methoxyphenyl)-2-(methylsulfonyl)ethan-1-amine of formula (1') or of formula (1") is between 0.5 and 1.5.

6. The process according to claim 1, further comprising hot-triturating the N-formyl leucine salt of 1-(3-ethoxy-4-methoxyphenyl)-2-(methylsulfonyl)ethan-1-amine of formula (4) in a solvent after the optically resolving step.

7. The process according to claim 1, in which the solvent of the optically resolving step is an alcohol.

8. The process according to claim 7, wherein the alcohol is selected from the group consisting of methanol, ethanol, 2-propanol, 1-butanol, 2-butanol, and tert-butanol, or mixtures thereof.

9. The process according to claim 1, further comprising deblocking the enantiomerically pure salt of formula (4) prepared in the optically resolving step to yield an enantiomerically pure 1-(3-ethoxy-4-methoxyphenyl)-2-(methylsulfonyl)ethan-1-amine of formula (1):

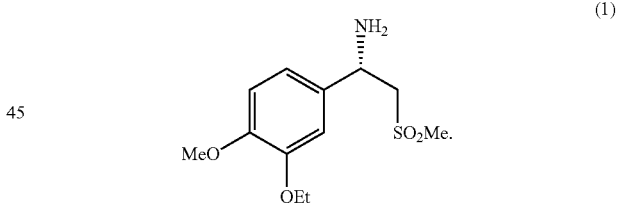

10. The process according to claim 1, further comprising reacting N-formyl leucine salt of formula (4) with N-(1,3-dioxo-1,3-dihydroisobenzofuran-4-yl)acetamide of formula (5) to produce an enantiomerically pure 1,3-dioxoisoindolin-4-ylacetamide of formula (6), a co-crystal, a solvate thereof, or a hydrate thereof:

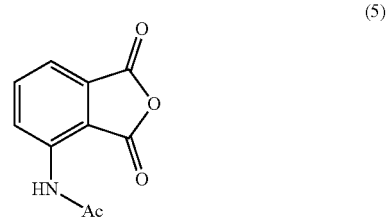

-continued

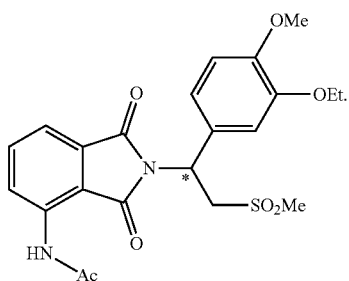
(6)

11. The process according to claim 10, further comprising crystallizing the enantiomerically pure 1,3-dioxoisoindolin-4-ylacetamide of formula (6) produced.

12. The process according to claim 6, further comprising deblocking the hot-triturated enantiomerically pure salt of formula (4) to yield an enantiomerically pure 1-(3-ethoxy-4-methoxyphenyl)-2-(methylsulfonyl)ethan-1-amine of formula (1):

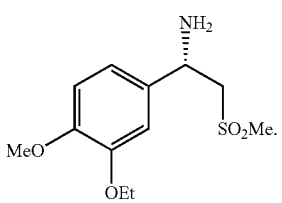
(1)

13. The process according to claim 9, further comprising reacting the enantiomerically pure 1-(3-ethoxy-4-methoxyphenyl)-2-(methylsulfonyl)ethan-1-amine (1) with N-(1,3-dioxo-1,3-dihydroisobenzofuran-4-yl)acetamide of formula (5) to produce an enantiomerically pure 1,3-dioxoisoindolin-4-ylacetamide of formula (6), a co-crystal, a solvate or a hydrate thereof:

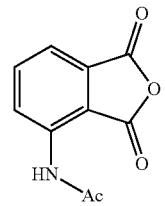
(5)

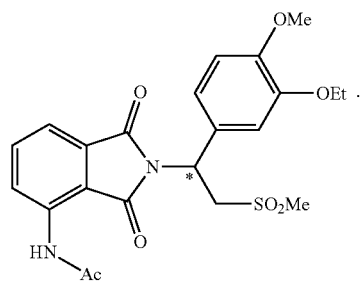
(6)

14. The process according to claim 13, further comprising crystallizing the enantiomerically pure 1,3-dioxoisoindolin-4-ylacetamide of formula (6) produced.

* * * * *